(12) United States Patent
Dent

(10) Patent No.: US 11,600,395 B1
(45) Date of Patent: Mar. 7, 2023

(54) SECURE PATIENT ACCESS VIA HEALTHCARE SERVICE PROVIDER SPECIFIC WIRELESS ACCESS POINT

(71) Applicant: HealthLynked Corp., Naples, FL (US)

(72) Inventor: Michael Thomas Dent, Naples, FL (US)

(73) Assignee: HealthLynked Corp., Naples, FL (US)

( * ) Notice: Subject to any disclaimer, the term of this patent is extended or adjusted under 35 U.S.C. 154(b) by 309 days.

(21) Appl. No.: 16/812,033

(22) Filed: Mar. 6, 2020

Related U.S. Application Data

(60) Provisional application No. 62/814,836, filed on Mar. 6, 2019.

(51) Int. Cl.
| | |
|---|---|
| *H04W 12/63* | (2021.01) |
| *G16H 80/00* | (2018.01) |
| *G16H 10/60* | (2018.01) |
| *H04W 4/021* | (2018.01) |
| *H04W 12/08* | (2021.01) |

(52) U.S. Cl.
CPC ............. *G16H 80/00* (2018.01); *G16H 10/60* (2018.01); *H04W 4/021* (2013.01); *H04W 12/08* (2013.01); *H04W 12/63* (2021.01)

(58) Field of Classification Search
CPC ..... H04W 12/63; H04W 4/021; H04W 12/08; G06F 16/90335
See application file for complete search history.

(56) References Cited

U.S. PATENT DOCUMENTS

| | | | |
|---|---|---|---|
| 2012/0305644 A1 | 12/2012 | Daniels, Jr. | |
| 2015/0237519 A1* | 8/2015 | Ghai | H04L 63/0892 370/252 |
| 2016/0302210 A1 | 10/2016 | Thornton | |
| 2016/0374776 A1 | 12/2016 | Spencer | |
| 2017/0329921 A1* | 11/2017 | Willard | G16H 40/67 |
| 2020/0258609 A1* | 8/2020 | McMaster | G16H 10/40 |

* cited by examiner

*Primary Examiner* — Anez C Ebrahim
(74) *Attorney, Agent, or Firm* — Sheppard Mullin Richter & Hampton LLP

(57) ABSTRACT

Systems and methods for providing a health care service provider specific wireless access point that facilitates secure communication between a patient, provider, and/or third-party service. Patient devices may connect to the healthcare service provider (HSP) wireless access point or "hub" when they are in range of the hub (e.g., when in a doctor's office waiting room). The wireless access point may be also configured to detect the presence of a patient device. In various implementations, the wireless access point may be configured to obtain identifying information of patient devices and send the information to a server. The server may be configured to use the information to create or update a profile for the patient associated with a patient device. The profile may be updated by additional information derived from the patient's interaction with the network, provider input, and/or by the patient updating their profile or inputting additional information.

13 Claims, 7 Drawing Sheets

SECURE PATIENT ACCESS VIA HEALTHCARE SERVICE PROVIDER SPECIFIC WIRELESS ACCESS POINT

CROSS-REFERENCE TO RELATED APPLICATIONS

This application claims the benefit of U.S. Provisional Patent Application Ser. No. 62/814,836, entitled "SECURE PATIENT ACCESS VIA HEALTH CARE SERVICE PROVIDER SPECIFIC WIRELESS ACCESS POINT", filed Mar. 6, 2019, which is hereby incorporated herein by reference in its entirety

FIELD OF THE INVENTION

The invention relates to a health care service provider specific wireless access point that facilitates secure communication between a patient, provider, and/or third-party service.

BACKGROUND OF THE INVENTION

Traditional check-in procedures at health care facilities (e.g., a doctors' office) typically involve the use of manual processes and oral disclosure between the patient and the doctors' staff to identify patients, coordinate patients' scheduling with the doctor, and orally calling patients when the doctor is ready to see them. Traditional patient check-in involves patients presenting themselves at the check-in desk to a receptionist. The receptionist has the patient sign in, provide updated insurance information, and provide forms for the patient to fill out for their initial visit or to update their existing medical information for the healthcare provider they are scheduled to see. In addition to being time/resource consuming, these manual/oral systems may risk the disclosure of personal health information to other patients in the waiting room. The use of these manual/oral systems also often results in unduly long wait or appointment times, as patients and staff may not be aware of and monitor how long a patient has been waiting or the total time a patient may spend in the office. Conventional systems for managing the arrival of patients at healthcare service provider facilities suffer from these and other drawbacks.

SUMMARY OF THE INVENTION

Various embodiments of the present disclosure may include systems, methods, and non-transitory computer readable media configured to provide a health care service provider specific wireless access point that facilitates secure communication between a patient, provider, and/or third-party service. Patient devices may connect to the healthcare service provider (HSP) wireless access point or "hub" when they are in range of the hub (e.g., when in a doctor's office waiting room). Communications between patient devices and the hub may use HIPAA compliant security. The hub may include one or more wireless access points that are separate from (but connected to), or part of, a router, which may connect to one or more networks. The router may communicate with one or more servers to send/receive information to/from a server. The server may aggregate, and process information received from a number of wireless access points. The server may be under control of a network service provider that makes the hubs available and performs services and functions described herein. By logging in to a provider's Wi-Fi network, the patient has Wi-Fi access, and the system can interact with the patient via the patient device.

In various implementations, the wireless access point may be configured to detect the presence of a patient device. For example, in implementations where the wireless access point acts as a Wi-Fi hub, the wireless access point may be configured to detect when the patient device enters the wireless range of the hub. The wireless access point may also be configured to detect the patient device when the patient device manually logs onto the WAP. In various implementations, the wireless access point may be configured to obtain identifying information of patient devices and send the information to server. The server may be configured to use the information to create or update a profile for the patient associated with a patient device. The profile may be updated by additional information derived from the patient's interaction with the network, provider input, and/or by the patient updating their profile or inputting additional information.

In various implementations, each HSP that participates in the network may display, in their waiting room, on a website or elsewhere, a QR code or other information that enables a patient to download a mobile application. The mobile application may have various functions. The mobile application enables a patient to create or update a profile, enter treatment or visit specific information, and/or other information. The patient entered data may be stored at the provider and/or at the network server. In various implementations, a function of the mobile application may be to present a display to a patient with prompts (or other patient interface elements) to facilitate the ability for the patient to input profile information. The patient input may be used to sign up or log in, create and/or update their profile and manage their medical information, search for providers, book and manage appointments, and/or otherwise interact with a provider. Healthcare-related social networking and/or other communication tools and features may also be made available via the patient application (or app) to enable a patient to communicate with family members, friends, other patients, and/or providers via the application in. The patient input may be sent to the server and associated with the patient device information to enhance the patient profile and associate the device information collected with the patient input to connect that information into the patient profile. A parent or other guardian may also create and manage profiles for children (e.g., under the age of 18).

In various implementations, one or more wireless access points may be located in an HSP facility. The wireless access point may comprise a Wi-Fi access point to patient devices that are in the facility. The first time a patient signs into the network they may be asked to enter their name, date of birth, email address, and/or other information. This may then grant the patient access to the internet through the Wi-Fi network. Practice locations may have their providers listed once the patient logs in and they will be asked to select the provider they are seeing today. This selection will then create a link between the patient and the healthcare service provider they are seeing for that visit. In certain implementations, the link between the patient and the healthcare service provider may comprise a communication channel between a patient device and a healthcare service provider device over the network. Once the link is established, the provider and patient may be able to share medical records and other healthcare related information securely through the network.

In various implementations, the wireless access point may collect and store other information about the patient. For example, information collected at or by a specific wireless access point may be stored on a server (or another computer storage device) at the HSP. In various implementations, patient information may be selectively accessible by a HSP facility, or other device, based on an authentication criteria. In some implementations, patient information may be accessible based on input provided by the patient device. Information may be stored by an HSP storage device or a remote storage device based on the information type. For example, protected health information may be stored on HSP storage device only. Other types information (i.e., patient profile information, analytical data, or other data associated with a patient or patient interactions) may be stored at a storage device associated with the network server in addition to, or instead of, at the HSP server. The determination of what information is stored where can be configured by the network operator, HSP administrator (or admin), or otherwise, and stored as rules within the system.

To illustrate, the wireless access point may determine when patient device has entered a geographic boundary, such as waiting area of an HSP facility. In various implementations, the wireless access point, or some processing resource associated with the wireless access point, may determine the patient device location using a GPS signal received by the patient device or by triangulating the position of the patient device using a local area triangulation involving one or more other wireless access point, or other beacons. In various implementations, the wireless access point may store or receive as input a plurality of interactions with a patient device over a period of time. For example, a wireless access point may be configured to determine and store the time that a patient device is detected by the wireless access point, indicating for example when a patient has arrived at (or is in close proximity) to the HSP waiting room. The wireless access point may also be configured to determine and store the time at which a patient departs the HSP office. This, and other time-related information that can be collected by the wireless access point may be used to determine useful statistics, such as how long a patient waits to be treated, overall time from when a patient arrives until they leave, how many patients are in a waiting room at a given time, and/or other information that may be relevant to the patient's visit and/or treatment history.

From the provider perspective, the system provides many features, functions, and advantages. Providers may include one or more wireless access points or hubs in their facility or facilities. By offering patient's free Wi-Fi, they can encourage patients to log-in and interact with the system. By autodetecting the presence of patients, the provider can provide a simpler, more effective check-in process, determine waiting times, and obtain other analytic information about patient interactions. A provider can upload list of their patients, so the wireless access point can more easily identify and track which patients have come in for a visit. The system also enables HIPAA secure messaging between the doctor and patient via the applications and the network.

These and other objects, features, and characteristics of the system and/or method disclosed herein, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

BRIEF DESCRIPTION OF THE DRAWINGS

The drawings are provided for purposes of illustration only and merely depict typical or example implementations. These drawings are provided to facilitate the reader's understanding and shall not be considered limiting of the breadth, scope, or applicability of the disclosure. For clarity and ease of illustration, these drawings are not necessarily drawn to scale.

DESCRIPTION OF THE INVENTION

It will be appreciated by those having skill in the art that the implementations described herein may be practiced without these specific details or with an equivalent arrangement. In various instances, well-known structures and devices are shown in block diagram form to avoid unnecessarily obscuring the implementations.

Example System Architecture

Figure 1:
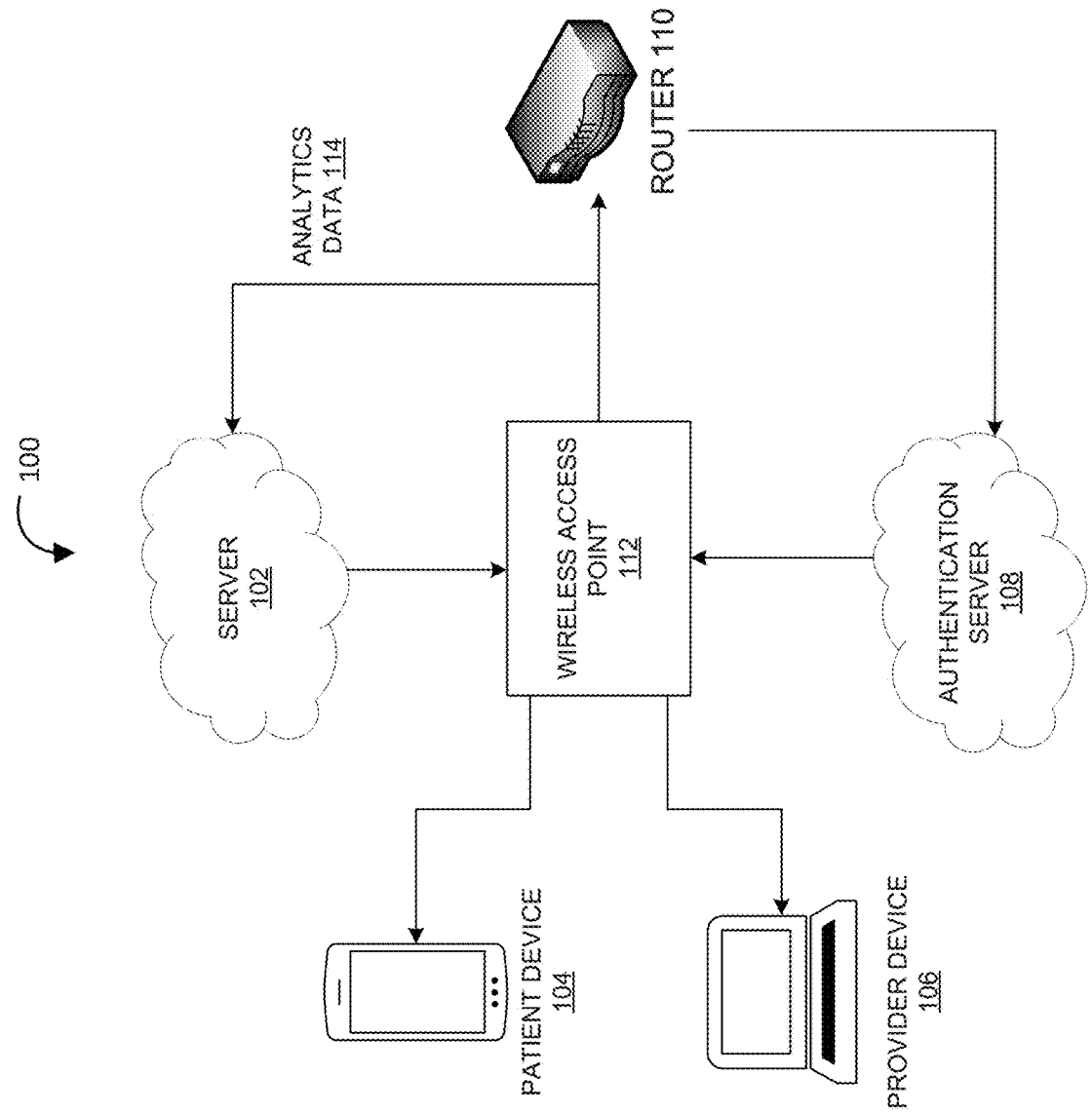
FIG. 1 illustrates a block diagram of an example of a network topology configured to provide a health care service provider specific wireless access point that facilitates secure communication between a patient, provider, and/or third-party service, in accordance with one or more implementations of the invention.

FIG. 1 illustrates a block diagram of an example network topology 100 configured to provide a health care service provider specific wireless access point that facilitates secure communication between a patient, provider, and/or third-party service, in accordance with one or more implementations of the invention. In various implementations, network architecture 100 may comprise a server 102, one or more patient devices 104 (also interchangeably referred to herein as patient devices 104, patient device(s) 104, or patient device 104 for convenience), one or more provider devices 106, an authentication server 108, a router 110, one or more wireless access points 112, and/or other components.

One aspect of the invention relates to providing a healthcare service provider (HSP) wireless access point 112 or "hub." The hub may include one or more WAPs 112 that are separate from (but connected to), or part of, a router 110, which may connect to one or more networks, such as a network illustrated in FIG. 1. Patient devices 104 (e.g., mobile phones, tablets, and/or other devices) may connect to the WAP 112 when they are in range of the hub (e.g., when in a doctor's office waiting room). Communications between the patient devices 104 and the WAP 112 may use HIPAA compliant security. The router 110 may communicate with one or more servers 102 to send/receive information to/from a server 102. In some embodiments, a plurality of WAP's 112 may connect to a common server 102 to form a network. The server 102 may aggregate, and process information received from a number of HSP WAPs 112 and patient's in-home WAPs (as detailed further below). The server 102 may be under control of a network service provider that makes the hubs available and performs services and functions described herein. The server 102 may be configured to receive and store analytics data 114, including at least medical information and patient interactions. As detailed below, by logging in to a provider's Wi-Fi network, the patient has Wi-Fi access, and the system can interact with the patient via the patient device.

In accordance with the embodiments described herein, one or more provider devices 106 may connect to one or more networks to communicate, or otherwise receive information from one or more patient devices 104 or server 102 via one or more WAP's. In various implementations, an authentication server 108 may be used to facilitate secure communications between the patient device 104 and provider device 106. In some implementations, communications between the patient device 104 and provider device 106 may comprise HIPAA-compliant protocols such as HL7-FHIR. As described herein, an authentication server 108 may be configured to permit or refuse access to the network and/or medical information.

In various implementations, WAP 112 may be configured to detect the presence of the patient device. For example, in implementations where the WAP 112 acts as a Wi-Fi hub, WAP 112 may be configured to detect when the patient device enters the wireless range of the hub. In various implementations, WAP 112 may be configured to detect the patient device when the patient device manually logs onto the WAP. For example, an operator of the patient device may provide log in credentials associated with the user profile in order to access the WAP. In some implementations, and as discussed further herein, the patient device may be detected upon entering a geographic boundary associated with a healthcare service provider facility. In certain implementations, the patient device may exchange identification or profile information to the WAP as a prerequisite of being detected by the WAP.

For example, WAP 112 may be configured to obtain the MAC address and/or other identifying information of patient devices and send the MAC address and/or other identifying information to server 102. Server 102 may be configured to use the MAC address and/or other identifying information to create or update a profile for the patient associated with a patient device 104. The profile may or may not have sufficient information initially to identify the patient specifically, but can be sufficient to identity the patient device 104. In situations where the same patient may revisit the provider or different providers that are part of the network and each of which providers have an WAP, such as WAP 112, at their office, the profile information can be used to recognize the same device. The profile may be updated by additional information derived from the patient's interaction with the network, provider input, and/or by the patient updating their profile or inputting additional information. For example, in the situation where the WAP is located in the waiting room of a physician's office, the WAP may be configured to detect the presence of a patient's device in the waiting room. The WAP may be configured to identify the MAC address of the patient's device and obtain additional information available from the patient device.

In various implementations, each HSP that participates in the network may display, in their waiting room, on a website or elsewhere, a QR code or other information that enables a patient to download a mobile application. The mobile application may have various functions. The mobile application enables a patient to create or update a profile, enter treatment or visit specific information, and/or other information. The patient entered data may be stored at the provider and/or at the network server.

In various implementations, a function of the mobile application may be to present a display to a patient with prompts (or other patient interface elements) to facilitate the ability for the patient to input profile information. The patient input may be used to sign up or log in, create and/or update their profile and manage their medical information, search for providers, book and manage appointments, and/or otherwise interact with a provider. Healthcare-related social networking and/or other communication tools and features may also be made available via the patient application (or app) to enable a patient to communicate with family members, friends, other patients, and/or providers via the application in. The patient input may be sent to the server and associated with the patient device information to enhance the patient profile and associate the device information collected by the HSP WAP 112 with the patient input to connect that information into the patient profile. As detailed further below, a parent or other guardian can create and manage profiles for children (e.g., under the age of 18).

Figure 2:
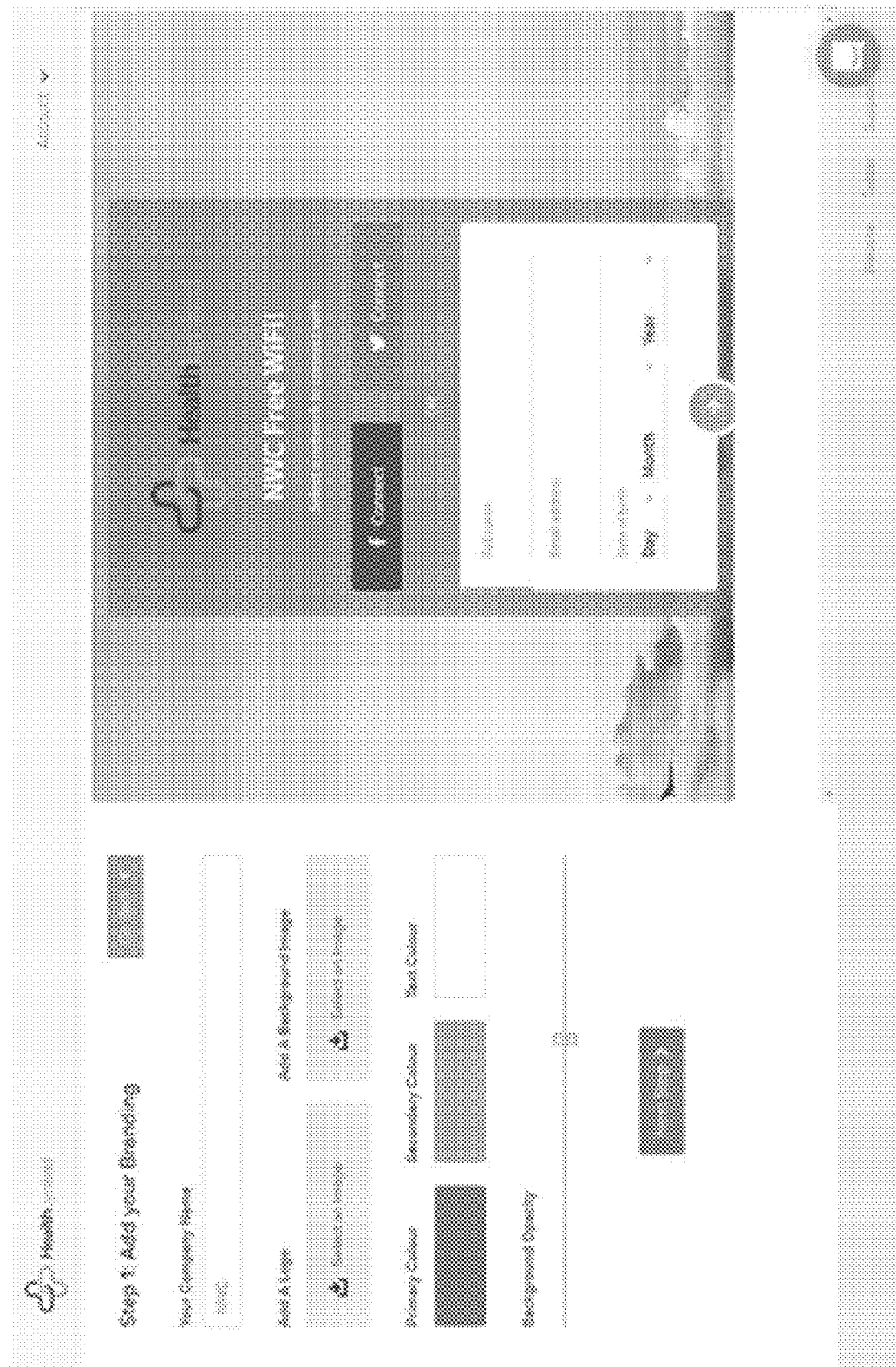
FIG. 2 illustrates an example of a healthcare service provider set-up screen, in accordance with one or more implementations of the invention.
Figure 3:
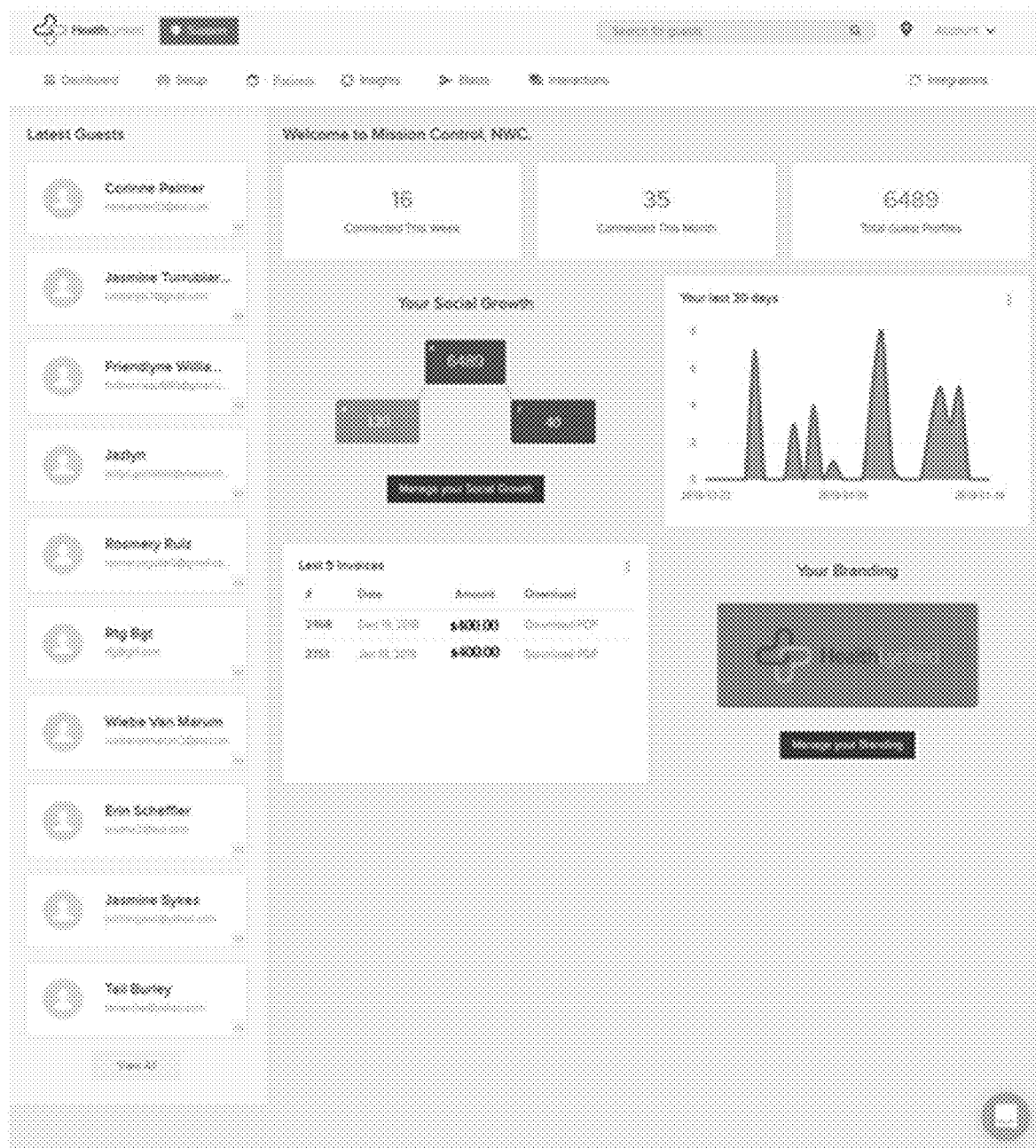
FIG. 3 illustrates an example of provider dashboard that enables a healthcare service provider to select from various functions (e.g., setup, patients, insights, communications, analytics, etc.), in accordance with one or more implementations of the invention.
Figure 4:
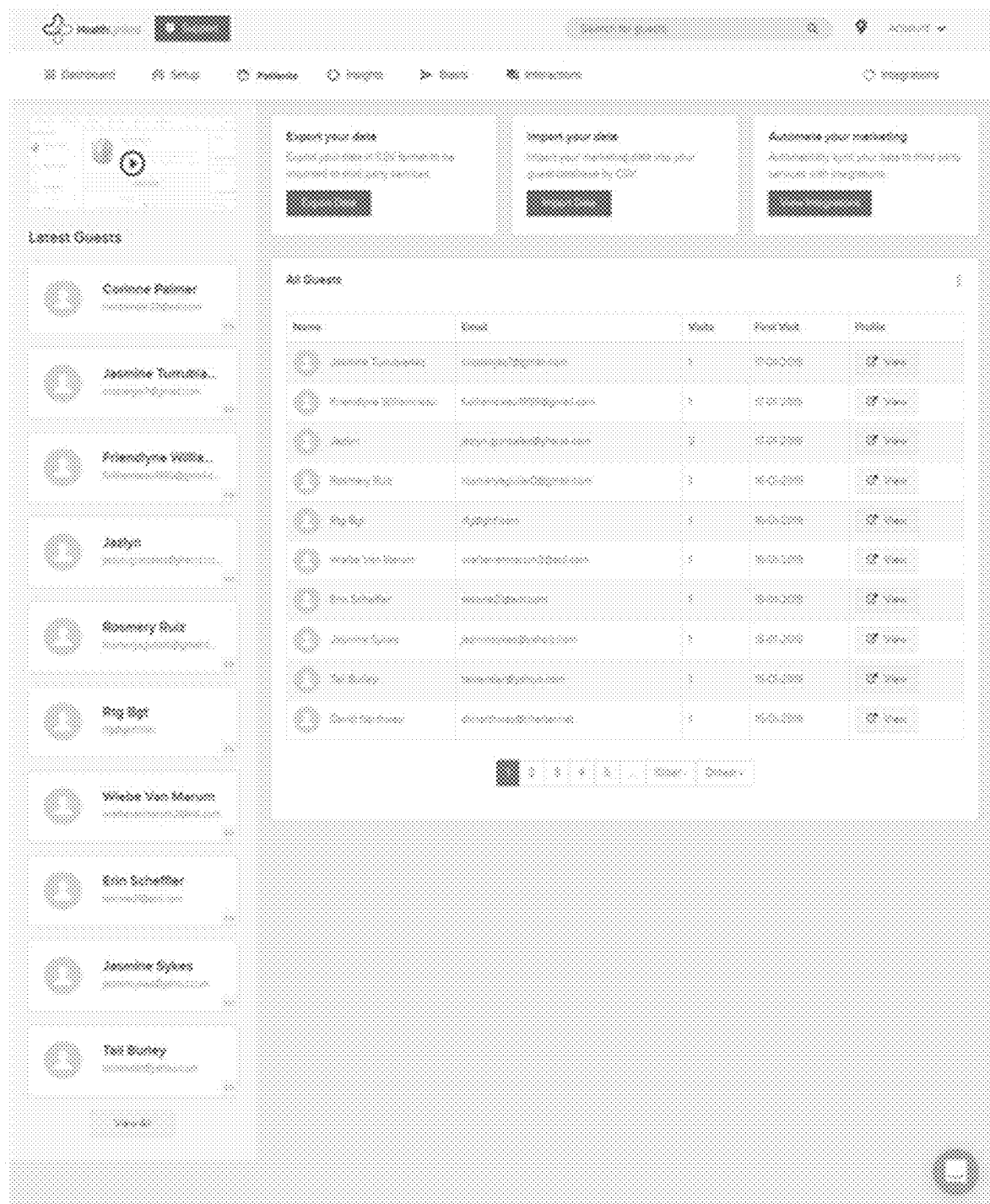
FIG. 4 illustrates an example of an interface configured to provide various support features, in accordance with one or more implementations of the invention.
Figure 5:
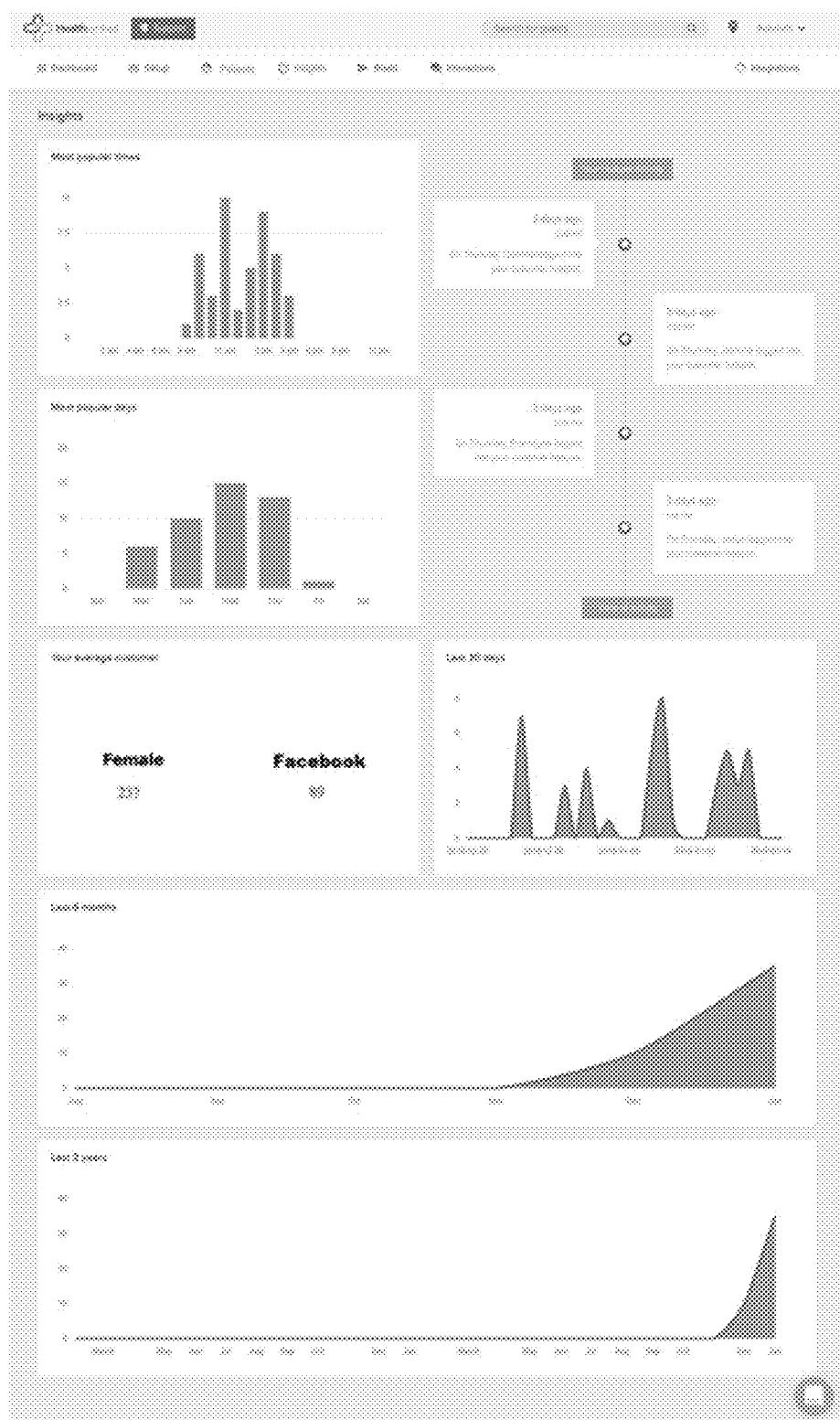
FIG. 5 illustrates an example of an interface configured to depict analytics available via the system, in accordance with one or more implementations of the invention.
Figure 6:
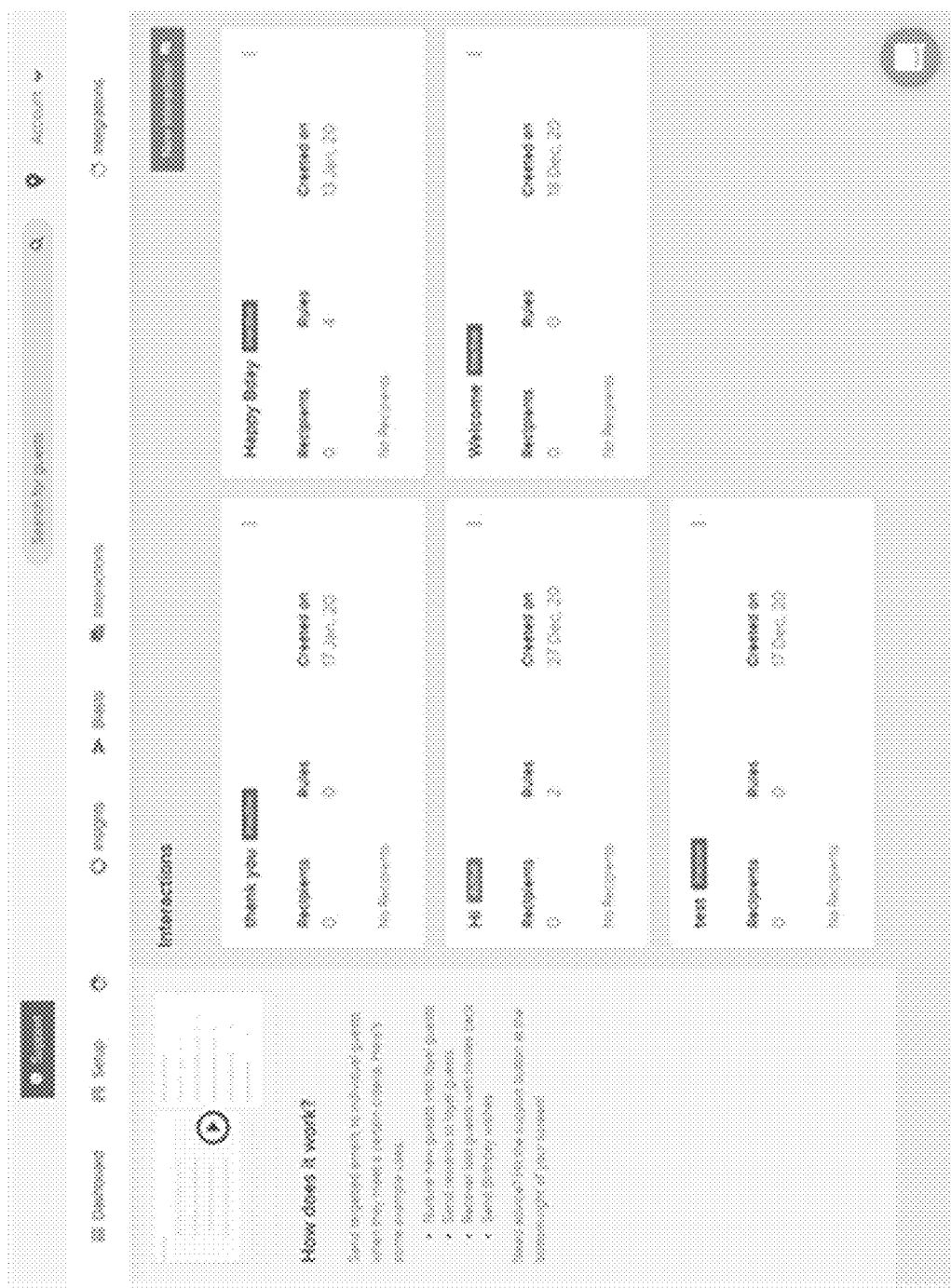
FIG. 6 illustrates an example of an interface through which a provider may create rules for messages to patients (greetings, reminders, etc.), in accordance with one or more implementations of the invention.

In various implementations, the mobile application may be configured to interface with a healthcare service provider dashboard accessible by the healthcare service provider. The healthcare service provider dashboard may comprise a series of interfaces with various functionality. FIG. 2 illustrates an example of a healthcare service provider set-up screen, in accordance with one or more implementations of the invention. FIG. 3 illustrates an example of provider dashboard that enables a healthcare service provider to select from various functions (e.g., setup, patients, insights, communications, analytics, etc.), in accordance with one or more implementations of the invention. FIG. 4 illustrates an example of an interface configured to provide various support features, in accordance with one or more implementations of the invention. For example, the various support features may enable a provider to import/export data, create automated marketing, see recent patients and/or other patient information, and/or perform one or more other actions enabled by the system. FIG. 5 illustrates an example of an interface configured to depict analytics available via the system, in accordance with one or more implementations of the invention. FIG. 6 illustrates an example of an interface through which a provider may create rules for messages to patients (greetings, reminders, etc.), in accordance with one or more implementations of the invention. For example, these rules may be easily customized and, through AI and/or machine learning, be updated and refined over time. These and/or other interfaces may be provided via the healthcare service provider dashboard to enable the healthcare service provider to interact with the system.

In various implementations, one or more WAPs 112 may be located in an HSP facility. In various implementations, the WAP 112 may comprise a Wi-Fi access point to patient devices 104 that are in the facility. The first time a patient signs into the network they may be asked to enter their name, date of birth, email address, and/or other information. This may then grant the patient access to the internet through the Wi-Fi network. Practice locations will have their providers listed once the patient logs in and they will be asked to select the provider they are seeing today. This selection will then create a link between the patient and the healthcare service provider they are seeing for that visit. In certain implementations, the link between the patient and the healthcare service provider may comprise a communication channel between a patient device and a healthcare service provider device over the network. Once the link is established, the provider and patient may be able to share medical records and other healthcare related information securely through the network.

In some implementations, the one or more WAPs 112 may autodetect the presence of the patient device 104, or the patient can log in to indicate their presence at the provider facility. For example, the WAP 112 may autodetect the presence of the patient device 104 when it is within range of the WAP 112 or within a defined boundary, such as a waiting area of an HSP facility. In some implementations, patients may log into the application via an email or social media connectivity. In some implementations, various biometric identifiers can be used to facilitate log-in.

In various implementations, the one or more WAPs 112 may be configured to recognize a patient member each time they return to the office (or another office in the network) so that a patient need not fill out log information for each visit. Rather the system may be configured to detect their presence, check them in, and the provider's staff can welcome the patient by name. In some embodiments, a patient device 104 may be detected through zero touch permission or auto sensing. For example, the one or more WAPs 112 may be configured to detect the presence of patient devices 104 even if the patients do not log into the HSP's Wi-Fi. This allows the system to confirm a patient has made an office visit even if they do not sign in to the Wi-Fi.

According to another aspect of the invention, a WAP may collect and store other information about the patient. As discussed herein, information collected at or by a specific WAP may be stored on a server (or another computer storage device) at the HSP. In various implementations, patient information may be selectively accessible by a HSP facility, or other device, based on an authentication criteria. In some implementations, patient information may be accessible based on input provided by the patient device 104.

Information may be stored by an HSP storage device or a remote storage device based on the information type. For example, protected health information may be stored on HSP storage device only. Other types information (i.e., patient profile information, analytical data as described herein, or other data associated with a patient or patient interactions) may be stored at a storage device associated with the network server in addition to, or instead of, at the HSP server. These are non-limiting examples of where information may be stored. Information may be stored on, for example, on a distributed server. The determination of what information is stored where can be configured by the network operator, HSP administrator (or admin), or otherwise, and stored as rules within the system.

For example, a WAP 112 may determine and store a timestamp of the detection, authentication of, or other instance involving the patient device 104 by the WAP 112. To illustrate, the WAP may determine when patient device 104 has entered a geographic boundary, such as waiting area of an HSP facility. In various implementations, the WAP 112, or some processing resource associated with the WAP 112, may determine the patient device location using a GPS signal received by the patient device or by triangulating the position of the patient device using a local area triangulation involving one or more other WAPs 112, or other beacons. In various implementations, WAP 112 may store or receive as input a plurality of interactions with a patient device 104 over a period of time. For example, WAPs 112 may be configured to determine and store the time that a patient device is detected by the WAP 112, indicating for example when a patient has arrived at (or is in close proximity) to the HSP waiting room. The HSP WAP may also determine and store the time at which a patient departs the HSP office. This, and other time-related information that can be collected by the WAP 112 may be used to determine useful statistics, such as how long a patient waits to be treated, overall time from when a patient arrives until they leave, how many patients are in a waiting room at a given time, and/or other information that may be relevant to the patient's visit and/or treatment history.

For example, by using multiple (e.g., three) provider specific WAPS 112 located at different but known locations within a provider's facility, the system can use triangulation or other techniques to track a patient location within the facility and a time associated with those locations. Determining location and temporal metrics associated with the patient device enables more useful statistics, including for example, the time at which a patient arrives, the wait time in a waiting room, the time at which a patient arrives in a treatment room, the time a patient moves to another location in the facility, etc. This information can be used to determine individual patient treatment times. Additionally, the information can be aggregated for multiple patients to determine average times for various activities. In implementations, this information may also be sent to and stored by the network server.

According to another feature of the invention, the current average wait time that exists at a given HSP facility and/or the number of patients waiting can be determined and sent to the applications/devices of patients who have upcoming appointments to assist them in better timing their arrivals. For example, using an artificial intelligence algorithm or machine learning model, the system may calculate a current wait-time, determine the number of other waiting patients, determine a patient's current location (via a geolocation technology associated with the patient's device and/or app), obtain traffic information from a third-party database, and predict the amount of time it will take the patient to arrive at the provider facility. Based on the determined wait time and other parameters, the system may determine an optimum time for the patient to depart from a specified address in order to arrive at a HSP facility in time for a scheduled appointment. In embodiments, a WAP may provide a notification to prompt the departure.

Upon a patient's arrival at the HSP facility, a patient device 104 may check in via an application to supplement the information determined by the WAP. For example, the patient can input specific visit information, such as the nature of treatment, a scheduled healthcare service provider, or other specialist with whom the patient has the appointment, and/or other visit specific information. This information can be collected, transmitted to the server, and stored in association with the patient's profile or a record associated with the patient separate from the profile. In various implementations, supplemental or specific visit information may be selectively stored and accessed based on a privacy setting or whether the information relates to the nature of a scheduled medical visit.

In implementations, once a patient arrives in a waiting room and the patient device 104 is detected, the system may prompt the user to provide certain information about their visit (e.g., the name of the doctor they are seeing, information about their medical issues, etc.). The system may process the information, such as the doctor's name received as input by the patient device 104, to create a link in the patient's profile with that of the doctor to facilitate secure interaction between them. The existence or occurrence of a link, for example, may be graphically displayed on a health care provider device. In various implementations, each provider at one or more facilities may have a profile stored on the system.

Using the GPS or other location determining capabilities of the patient device, one or more location specific features may be provided. For example, based on the determined location of the patient device 104, the application can access a database of pharmacies, labs, and/or other business locations that may be related to a patient treatment or visit. Using a geolocation technology, the application may identify the nearest business. With other information that may be stored in the database (e.g., hours of operation) the application may provide information or recommendations that take into account features other than just proximity. The patient may specify one or more parameters (e.g., type of business, proximity, hours of operation, products and/or services provided, and/or other information) and the application may search for and return a list of results to the patients via the application interface. The patient may select a business from the list and may then interact directly with that business via the application or otherwise.

In various implementations, a patient may manage medication information via the application. The patient may enter the medications that the patient is currently taking. This information may be stored as part of or separate from the patient profile. If a device is granted access to this information, in accordance with the disclosure, the server may access a database to view the patient's history of interactions (i.e., visits, purchases) with one or more businesses (i.e., a pharmacy).

In various implementations, a patient may manage medical history and/or other record information via the application. For example, the application operating on the patient device may enable a patient to upload a medical record in digital format, provide metadata tags, view it, provide selective access to it for a provider and/or delete it.

For any information that may need to be, or for which the patient desires it to be stored separately from the patient profile record, this information may be securely stored. Via the application, the patient may selectively share the securely stored information with one or more providers, businesses, and/or others, at the patient's discretion or based on an authentication criteria. The patient can provide sharing parameters (e.g., for how long the information is shared, etc.) to control the sharing of sensitive information.

When a patient visits a specific HSP, the HSP WAP may detect the patient's presence and prompt the patient via the app to share certain records or other information related to the purpose of the visit. The patient can selectively permit access to some or all of the information and other sharing parameters via the application. The patient may also selectively share their medical information or portions of it with others (family members or other service providers) through the application.

According to one aspect of the invention, the HSP may have an application that interacts with the system. When the HSP WAP determines the presence of a patient at the HSP facility, information about the patient and the visit may be displayed via the provider application. For example, the provider application may enable a provider to see a high-level (e.g., metadata level) view of an archive of the patient's medical records, without seeing or having access to the entire record, unless permission is granted by the patient.

According to another aspect of the invention, a profile can be created by a first person ("a profile creator") on behalf of another individual ("a profile subject"). For example, a parent can create a profile for a child or someone less than 18 years of age. The profile record as stored may include a designation of the profile creator and the profile subject. The system will treat the profile as being owned and controlled by the profile creator. This enables the profile creator to update, control access to and the sharing of information associated with the profile, and/or other functionality. Upon the occurrence of an event or other trigger, the profile subject may become the profile owner. For example, if the profile subject turns 18 years of age, the profile subject may be able to claim ownership of their profile. When a profile subject claims ownership of a profile, the system record is updated to reflect the profile subject as the record owner and terminates the profile creator's rights as profile owner. From that point forward, the profile creator may be prevented from performing functions for that profile for which only the profile owner can perform.

According to another aspect of the invention, the system may include an artificial intelligence (and/or machine learning) module and use network information to make personal health care recommendations to patient members. For example, the system may store a set of rules that are used to create reminders (e.g., a reminder to obtain a mammogram) based on a user's profile, medical records and/or other data in the system. If a patient is undergoing a series of treatments, the system can provide reminders and/or recommendations that are treatment-specific.

From the provider perspective, the system provides many features, functions, and advantages. Providers may locate one or more HSP WAPs or hubs in their facility or facilities. By offering patient's free Wi-Fi, they can encourage patients to log-in and interact with the system. By autodetecting the presence of patients, the provider can provide a simpler, more effective check-in process, determine waiting times, and obtain other analytic information about patient interactions. A provider can upload list of their patients, so the WAP can more easily identify and track which patients have come in for a visit. The system also enables HIPAA secure messaging between the doctor and patient via the applications and the network. This is not typically feasible with SMS messaging. In implementations, a patient may opt-in to receive certain notifications from the provider via the application.

The patient and provider applications can also include a telemedicine feature to enable secure, HIPAA compliant communications, even when the patient is at home, by using a hub or WAP in the patient's home. In an embodiment, communications may use the HL7-FHIR (Fast Healthcare Interoperability Resources) protocol.

Through this combination of features, the system may operate as a secure, HIPPA compliant social network for healthcare, connecting patients with the doctors they choose.

In addition to this, the system acts to create a PHR (personal health record) for patient members that allows their medical information to move with them outside the regulations of HIPAA. The system can also provide personal healthcare recommendations based on each individual member's specific medical history.

The system may maintain profiles for different types of providers, including: (i) out of network providers who have not claimed their online profile and (ii) in-network providers. In implementations, in-network providers may be able to connect with patient members, access marketing services, allow patients to book appointments online, share medical records with their patients, and access practice analytics from the patient access hub device, while out of network providers have limited communication with a given patient device.

The network providers maintaining a WAP may derive many advantages in accordance with the disclosure. For example, the patient access HUB provides a great amount of detail to the medical providers such as: (i) number of patients seen that day by providers; (ii) how long patients waited; (iii) information on which days of the week and hours of each day are the busiest; (iv) ways to better manage their practice better based on these metrics; (v) social sharing; (vi) follow up surveys and reminders to patients via their mobile devices; (vii) ability to upload their patient list into their secure cloud database so that patients may be recognized on their initial log into to the Wi-Fi router; and/or other information that may be pertinent to a patient's interaction, experience, or history with a HSP or HSP facility.

When healthcare information is exchanged, it may need to be exchanged in a secure fashion. The traditional method is using an encryption called HL-7. The system described herein can utilize HL-7, a new improved encryption method called Patient HL7-FHIR, and/or other forms of encryption. For example, a WAP may use HL7-FHIR encryption in the a WAP or another type of patient access hub.

In an implementation of the disclosure, a WAP or another type of patient access hub may be maintained at a location remote to a HSP facility. For example, a WAP or another type of patient access hub may be provided to patient for use at the patient's home to facilitate the secure communication of medical information collected by medical devices at the patient's home. For example, in prior art systems, if a patient is using a wireless healthcare device (e.g., a Wi-Fi enabled device like a blood pressure monitor or glucometer at home), this information may be sent over standard internet services that does not meet the new HL7-FHIR standards. Alternatively, providing patients a WAP to connect with via in-home wireless devices, so that the wireless devices can transmit information a server via the in-home WAP (i.e., a network server, provider server or otherwise). In accordance with the disclosure, the in-home WAP may provide a network that is secure for transmitting real-time medical information from in-home medical devices to providers or elsewhere. This may enhance the ability to securely monitor patient members health information in real-time.

In addition to the network access hub technology, the system described herein can incorporate various healthcare algorithms that provide patients medical recommendations based on their specific medical history. For example, base algorithms may remind patients of such things as when they are due for their pap smear, MMG, and colonoscopy, etc., based on medical or visit information received from that patient's device. Further, these recommendations may be based on other patient profile information, such as the gender and age of the patient, along with a testing time interval recommended by the health care provider, prior test results, and family history.

The system may also enable improved interaction with other healthcare services, such as a diagnostic testing lab. For example, a WAP 112 may be provided in the facility of a diagnostics or clinical lab. In various implementations, the presence of a patient device 104 may be detected by WAP 112 as disclosed herein. In some implementations, the patient's treating physician, or a corresponding device, may be notified that the patient entered the lab. In some implementations, the notification indicating that the patient has entered the lab may be based on the patient's location, a schedule, or input received by a patient device 104 or a HSP device. Then, the lab may perform tests and transmit results securely and in real-time to the treating physician via the WAP. In some implementations, the transmission may occur directly from a lab WAP to an HSP device. In other implementations, the WAP may transmit testing information securely to a WAP, that is closer in proximity to the HSP device. In other implementations, the WAP may transmit testing information securely to a WAP that is already connected to an HSP device. In accordance with the disclosure herein, similar approaches may be used with in-home testing using a hub in the patient's home.

Additionally, if a patient being treated by a doctor needs a test, the doctor may schedule a time for the patient, send information to the patient's application directing the user where and when to go for the test, and provide other information about the test via the application.

In accordance with the embodiments disclosed herein, the ability of the hub device to detect the proximity of mobile devices can provide a level of security around healthcare payments at the time of service. For example, a patient's mobile device could make payments for healthcare services, but only when at the point of service (proximity and time) to provide an enhanced level of security around these transactions. According to another advantage of the network, the service provider may enable patients to call, message, or communicate with their healthcare service provider via a common number. Upon receipt of the call, an artificially intelligent bot can identify the patient and direct the patient's call to healthcare service providers the patient is attempting to connect with.

In various implementations, the functionality of the system provides unique search engine capability to perform more personalized and targeted search queries for patient searches. The system may use prior searches, profile information, known medical information, and/or other information gathered about the patient to help with determining key results. The system may use the individual's healthcare information when they ask a question that is medical related. For example, if a patient is on a medication with a known incidence of creating a rash, the system may know patient-specific information, make a query regarding the rash and would be able to use that intelligence to inform the patient that there is a high probability the rash is related to this medication. Knowing the patient's age, medical history, family history, and/or medications may provide a more meaningful response from the query.

Example Flowchart of Processes

Figure 7:
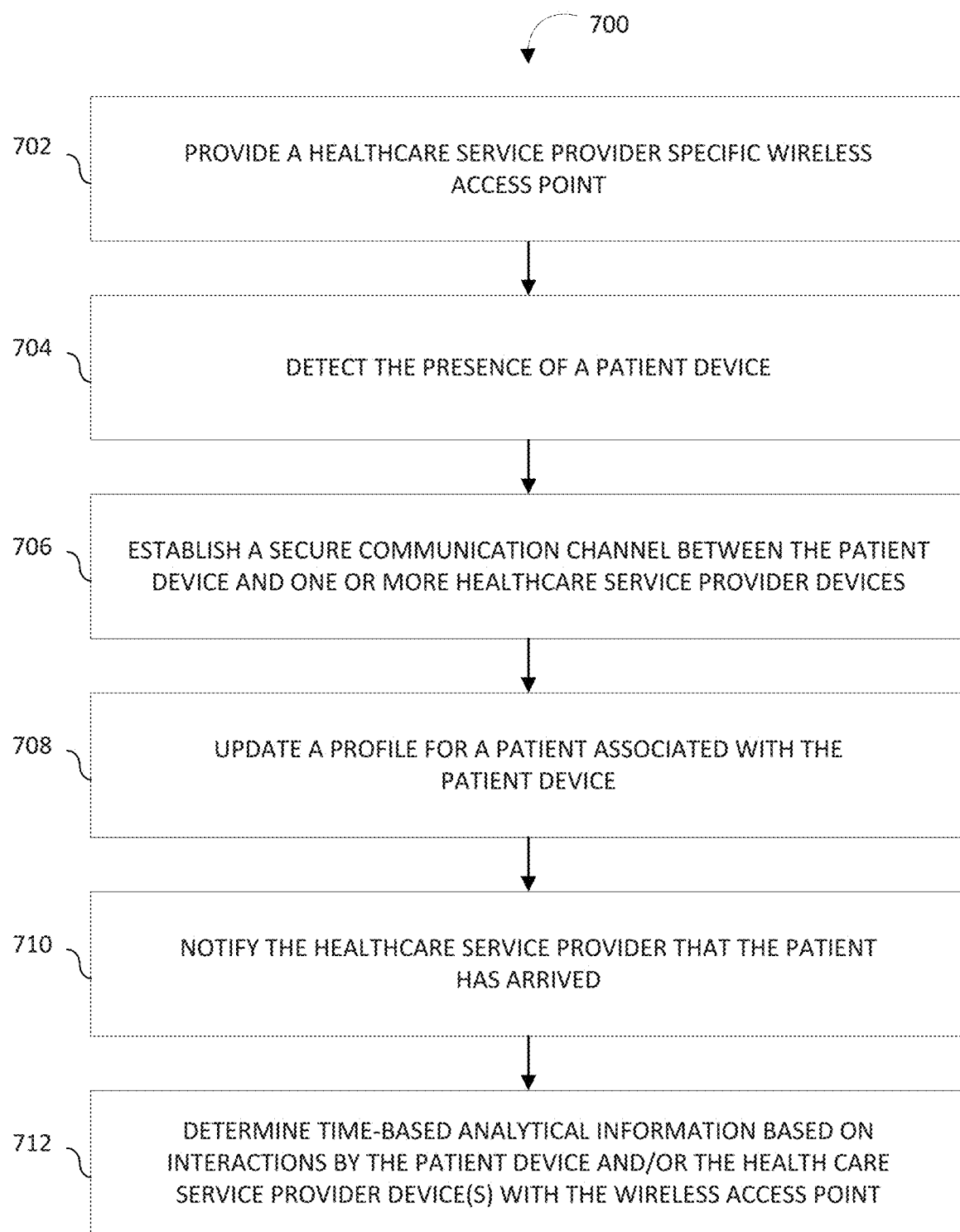
FIG. 7 illustrates an example of a process for providing a health care service provider specific wireless access point that facilitates secure communication between a patient, provider, and/or third-party services, in accordance with one or more implementations of the invention.

FIG. 7 illustrates an example of a process 700 for providing a health care service provider specific wireless access point that facilitates secure communication between a patient, provider, and/or third-party service, in accordance with one or more implementations of the invention. The operations of process 700 presented below are intended to be illustrative and, as such, should not be viewed as limiting. In some implementations, process 700 may be accomplished with one or more additional operations not described, and/or without one or more of the operations discussed. In some implementations, two or more of the operations may occur substantially simultaneously. The described operations may be accomplished using some or all of the system components described in detail above.

In some implementations, process 700 may be implemented in one or more processing devices (e.g., a digital processor, an analog processor, a digital circuit designed to process information, a central processing unit, a graphics processing unit, a microcontroller, an analog circuit designed to process information, a state machine, and/or other mechanisms for electronically processing information). For example, process 700 may be implemented by system 100 as described herein. The one or more processing devices may include one or more devices executing some or all of the operations of process 700 in response to instructions stored electronically on one or more electronic storage mediums. The one or more processing devices may include one or more devices configured through hardware, firmware, and/or software to be specifically designed for execution of one or more of the operations of process 700.

In an operation 702, process 700 may include providing a wireless access point at a facility of one or more healthcare service providers. For example, the wireless access point may comprise a healthcare service provider specific wireless access point. In various implementations, the wireless access point may comprise a router connected to one or more servers. In some implementations, multiple wireless access points may be located within and/or associated with the facility.

In an operation 704, process 700 may include electronically detecting the presence of a patient device within range of the wireless access point. In some implementations, electronically detecting the presence of a patient device within range of the wireless access point may comprise determining that the patient device has connected to the wireless access point via a Wi-Fi network of the facility of one or more healthcare service providers. In some implementations, electronically detecting the presence of a patient device within range of the wireless access point may comprise determining, based on GPS coordinates of the patient device, that the patient device is within a predefined geographic boundary associated with the facility of one or more healthcare service providers. In some implementations, electronically detecting the presence of a patient device within range of the wireless access point may comprise detecting the patient device by zero touch permission or auto sensing. In some implementations, electronically detecting the presence of a patient device within range of the wireless access point may comprise triangulating a geographic location of the patient device and determining that the triangulated geographic location is within a geographic boundary defined by the multiple wireless access points. For example, in implementations in which the facility comprises multiple wireless access points, the multiple wireless access points may be used to triangulate the geographic location of the patient device. One or multiple of the techniques described herein for detecting the presence of a patient device may be used to detect the presence of any single device within range of the wireless access point.

In an operation 706, process 700 may include establishing a secure communication channel between the patient device and a device of the one or more healthcare service providers. In various implementations, the secure communication channel may be automatically established responsive to the detection of the presence of the patient device. The secure communication channel may implement the HL7-FHIR protocol. In some implementations, the wireless access point may be utilized to receive, from the patient device, authorization for a device of the one or more healthcare service providers to selectively access medical information. For example, a patient may provide input via the secured communication channel indicating consent by the patient for the device of the one or more healthcare service providers to selectively access medical information related to the purpose of a medical appointment with the one or more healthcare service providers via the secured communication channel. In some implementations, the patient may provide the input via a mobile application associated with the one or more healthcare service providers. In some implementations, responsive to the detection of the patient device and/or the establishment of the secure communication channel, one or more notifications may be automatically displayed via the patient device. For example, a notification may be provided that includes a prompt for the patient to download or access a mobile application associated with the one or more healthcare service providers. The mobile application may, for example, enable a patient associated with the patient device to create or update a patient profile associated with the patient and/or enter treatment- or visit-specific information.

In an operation 708, process 700 may include updating a profile for a patient associated with the patient device responsive to the detection of the patient device and/or the establishment of the secure communication channel. For example, information identifying the patient device may be obtained and used to identify a profile for a patient associated with the patient device. The profile for the patient may then be updated based on interactions between the wireless access point and the patient device and/or one or more healthcare service provider devices.

In an operation 710, process 700 may include notifying the one or more healthcare service providers that the patient associated with the patient device has arrived. For example, a notification may be provided via the device of the one or more healthcare service providers responsive to the detection of the presence of the patient device within range of the wireless access point. The notification may include an indication that a patient associated with the patient device has arrived at the facility of one or more healthcare service providers. In some implementations, information identifying the patient device may be obtained and used to identify a profile for a patient associated with the patient device responsive to the detection of the patient device and/or the establishment of the secure communication channel. Based on the identified profile, a scheduled appointment for the patient with at least one of the one or more healthcare service providers may be identified. Responsive to the detection of the patient device and/or the establishment of the secure communication channel, the patient may be automatically checked in for the identified appointment.

In an operation 712, process 700 may include determining time-based analytical information based on interactions between the wireless access point and the patient device and/or the one or more healthcare service provider devices. In various implementations, a timestamp indicating a time at which the presence of patient device was detected may be obtained (and stored). Based on the timestamp and/or input received from a device of the one or more healthcare service providers, a wait time for the patient associated with the patient device may be calculated and provided to the one or more healthcare service providers via the device. In various implementations, a time at which the patient device leaves the facility of the one or more healthcare service providers may be determined. For example, a geographic location of the patient device may be triangulated (e.g., using the multiple wireless access points) and used to determine a time at which the patient device leaves the facility based on a determination that the geographic location is outside a geographic boundary associated with the facility. Based on the timestamp for the detection of the presence of the patient device and the determined time at which the patient device leaves the facility, an overall time for the appointment of the patient may be calculated and provided to the one or more healthcare providers.

The various processing operations and/or data flows depicted in FIG. 7 (and in the other drawing figures) are described in greater detail herein. The described operations may be accomplished using some or all of the system components described in detail above and, in some implementations, various operations may be performed in different sequences and various operations may be omitted. Additional operations may be performed along with some or all of the operations shown in the depicted flow diagrams. One or more operations may be performed simultaneously. Accordingly, the operations as illustrated (and described in greater detail below) are exemplary by nature and, as such, should not be viewed as limiting.

For purposes of explanation, numerous specific details are set forth in order to provide a thorough understanding of the description. It will be appreciated by those having skill in the art that the implementations described herein may be practiced without these specific details or with an equivalent arrangement. Accordingly, it is to be understood that the technology is not limited to the disclosed implementations, but, on the contrary, is intended to cover modifications and equivalent arrangements that are within the spirit and scope of the appended claims. For example, it is to be understood that the present technology contemplates that, to the extent possible, one or more features of any implementation can be combined with one or more features of any other implementation.

As disclosed herein, features consistent with the disclosure may be implemented via computer-hardware, software and/or firmware. For example, the systems disclosed herein may be embodied in various forms including, for example, a data processor, such as a computer that also includes a database, digital electronic circuitry, firmware, software, or in combinations of them. Further, while some of the disclosed implementations describe specific hardware components, systems and methods consistent with the innovations herein may be implemented with any combination of hardware, software and/or firmware. Moreover, the above-noted features and other aspects and principles of the innovations herein may be implemented in various environments. Such environments and related applications may be specially constructed for performing the various routines, processes and/or operations according to the invention or they may include a general-purpose computer or computing platform selectively activated or reconfigured by code to provide the necessary functionality. The processes disclosed herein are not inherently related to any particular computer, network, architecture, environment, or other apparatus, and may be implemented by a suitable combination of hardware, software, and/or firmware. For example, various general-purpose machines may be used with programs written in accordance with teachings of the invention, or it may be more convenient to construct a specialized apparatus or system to perform the required methods and techniques.

It should also be noted that the various logic and/or functions disclosed herein may be enabled using any number of combinations of hardware, firmware, and/or as data and/or instructions embodied in various machine-readable or computer-readable media, in terms of their behavioral, register transfer, logic component, and/or other characteristics. Computer-readable media in which such formatted data and/or instructions may be embodied include, but are not limited to, non-volatile storage media in various forms (e.g., optical, magnetic or semiconductor storage media) though again does not include transitory media. Unless the context clearly requires otherwise, throughout the description, the words "comprise," "comprising," and the like are to be construed in an inclusive sense as opposed to an exclusive or exhaustive sense; that is to say, in a sense of "including, but not limited to." Words using the singular or plural number also include the plural or singular number respectively.

Reference in this specification to "one implementation", "an implementation", "some implementations", "various implementations", "certain implementations", "other implementations", "one series of implementations", or the like means that a particular feature, design, structure, or characteristic described in connection with the implementation is included in at least one implementation of the disclosure. The appearances of, for example, the phrase "in one implementation" or "in an implementation" in various places in the specification are not necessarily all referring to the same implementation, nor are separate or alternative implementations mutually exclusive of other implementations. Moreover, whether or not there is express reference to an "implementation" or the like, various features are described, which may be variously combined and included in some implementations, but also variously omitted in other implementations. Similarly, various features are described that may be preferences or requirements for some implementations, but not other implementations.

The language used herein has been principally selected for readability and instructional purposes, and it may not have been selected to delineate or circumscribe the inventive subject matter. Other implementations, uses, and advantages of the invention will be apparent to those skilled in the art from consideration of the specification and practice of the invention disclosed herein. Although certain presently preferred implementations of the invention have been specifically described herein, it will be apparent to those skilled in the art to which the invention pertains that variations and modifications of the various implementations shown and described herein may be made without departing from the spirit and scope of the invention. Accordingly, it is intended that the invention be limited only to the extent required by the applicable rules of law.

What is claimed is:

1. A computer implemented method for providing a service provider specific wireless access point that facilitates secure communication between a customer, provider, and/or third-party services, the method comprising the operations of:

providing a wireless access point at a facility of one or more service providers, wherein the wireless access point comprises a router connected to one or more servers, wherein the facility of one or more service providers includes multiple wireless access points, the multiple wireless access points including the wireless access point;

electronically detecting the presence of a patient customer device within range of the wireless access point by:

triangulating a geographic location of the customer device using the multiple wireless access points, and determining that the triangulated geographic location is within a geographic boundary defined by the multiple wireless access points;

responsive to the detection of the presence of the customer device, establishing a secure communication channel between the customer device and a device of the one or more service providers;

triangulating a second geographic location of the customer device using the multiple wireless access points;

determining a time at which the customer device leaves the facility of the one or more service providers based on a determination that the second geographic location is outside the geographic boundary;

calculating an overall time for an appointment of the customer based on a timestamp for the detection of the presence of the customer device and the determined time at which the customer device leaves the facility; and causing the calculated overall time to be provided to the device of the one or more service providers.

2. The method of claim 1, wherein:

the service provider is a health care service provider;

the customer is a patient; and the customer device is a patient device.

3. The method of claim 2, the method further comprising:

obtaining a timestamp for the detection of the presence of the patient device;

calculating a wait time for a patient associated with the patient device based on the timestamp and input received from a device of the one or more healthcare service providers; and causing the calculated wait time to be provided to the device of the one or more healthcare service providers via the device.

4. The method of claim 2, wherein electronically detecting the presence of a patient device within range of the wireless access point comprises:

determining that the patient device has connected to the wireless access point via a Wi-Fi network of the facility of one or more healthcare service providers.

5. The method of claim 2, wherein electronically detecting the presence of a patient device within range of the wireless access point comprises:

determining, based on GPS coordinates of the patient device, that the patient device is within a predefined geographic boundary associated with the facility of one or more healthcare service providers.

6. The method of claim 2, wherein electronically detecting the presence of a patient device within range of the wireless access point comprises detecting the patient device by zero touch permission or auto sensing.

7. The method of claim 2, the method further comprising:

obtaining information identifying the patient device responsive to the detection of the presence of the patient device within range of the wireless access point;

identifying a profile for a patient associated with the patient device based on the information identifying the patient device; and updating the profile for the patient based on interactions between the wireless access point and the patient device or the device of the healthcare service provider device.

8. The method of claim 2, the method further comprising:

causing a notification to be provided via the device of the one or more healthcare service providers responsive to the detection of the presence of the patient device within range of the wireless access point, wherein the notification comprises an indication that a patient associated with the patient device has arrived at the facility of one or more healthcare service providers.

9. The method of claim 8, the method further comprising:

obtaining information identifying the patient device responsive to the detection of the presence of the patient device within range of the wireless access point;

identifying a profile for a patient associated with the patient device based on the information identifying the patient device;

determining that the patient has a scheduled appointment with at least one of the one or more healthcare service providers; and causing the patient to be automatically checked in for the appointment electronically responsive to the detection of the presence of the patient device within range of the wireless access point.

10. The method of claim 2, the method further comprising:

causing a notification to be displayed via the patient device, wherein the notification comprises a prompt to download or access a mobile application associated with the one or more healthcare service providers responsive to the detection of the presence of the patient device within range of the wireless access point.

11. The method of claim 10, wherein the mobile application enables a patient associated with the patient device to create or update a profile for the patient associated with the patient device and/or enter treatment- or visit-specific information.

12. The method of claim 2, wherein the secure communication channel implements the HL7-FHIR protocol.

13. The method of claim 2, the method further comprising:

receiving, from the patient device, authorization for the device of the one or more healthcare service providers to selectively access medical information related to the purpose of a medical appointment with the one or more healthcare service providers via the secure communication channel.

\* \* \* \* \*

UNITED STATES PATENT AND TRADEMARK OFFICE
CERTIFICATE OF CORRECTION

| | |
|---|---|
| PATENT NO. | : 11,600,395 B1 |
| APPLICATION NO. | : 16/812033 |
| DATED | : March 7, 2023 |
| INVENTOR(S) | : Michael Thomas Dent |

It is certified that error appears in the above-identified patent and that said Letters Patent is hereby corrected as shown below:

In the Claims

Column 16, Line 66, (Claim 1), change "of a patient customer" to --of a customer--;

Column 17, Lines 35-36, (Claim 3), change "service providers via the device." to --service providers.--;

Column 18, Lines 10-11, (Claim 7), change ""service provider device." to --service provider.--.

Signed and Sealed this
Thirteenth Day of June, 2023

Katherine Kelly Vidal
*Director of the United States Patent and Trademark Office*